(12) United States Patent
Acker et al.

(10) Patent No.: US 9,550,040 B2
(45) Date of Patent: *Jan. 24, 2017

(54) BREATHING APPARATUS DETECTION AND PURGING

(71) Applicant: Mallinckrodt Hospital Products IP Limited, Mulhuddart, Dublin (IE)

(72) Inventors: Jaron M. Acker, Madison, WI (US); Thomas Kohlmann, McFarland, WI (US)

(73) Assignee: Mallinckrodt Hospital Products IP Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 14/827,523

(22) Filed: Aug. 17, 2015

(65) Prior Publication Data

US 2015/0352311 A1    Dec. 10, 2015

Related U.S. Application Data

(63) Continuation of application No. 14/394,433, filed as application No. PCT/US2013/035079 on Apr. 3, 2013, (Continued)

(51) Int. Cl.
*A61M 16/12* (2006.01)
*A61M 16/06* (2006.01)
(Continued)

(52) U.S. Cl.
CPC ......... *A61M 16/12* (2013.01); *A61M 16/0003* (2014.02); *A61M 16/0051* (2013.01);
(Continued)

(58) Field of Classification Search
CPC .............. A61M 16/00; A61M 16/0051; A61M 16/0057–16/0072; A61M 16/0666–16/0677; A61M 16/10–16/104; A61M 16/12; A61M 16/20–16/205
See application file for complete search history.

(56) References Cited

U.S. PATENT DOCUMENTS 5,485,850 A    1/1996   Dietz
5,558,083 A    9/1996   Bathe et al.
(Continued)

FOREIGN PATENT DOCUMENTS

EP    0659445    6/1995
EP    0937479    8/1999
WO    WO 01/95972    12/2001

OTHER PUBLICATIONS

Final Office Action in U.S. Appl. No. 13/440,046, dated Mar. 1, 2013, 17 pages.
(Continued)

*Primary Examiner* — Rachel Young
(74) *Attorney, Agent, or Firm* — Servilla Whitney LLC

(57) ABSTRACT

Described are methods for safer nitric oxide delivery, as well as apparatuses for performing these methods. The methods may include detecting the presence or absence of a nasal cannula, and stopping the delivery of nitric oxide or providing an alert if the cannula is disconnected. The methods may also include purging the nasal cannula if it is reconnected after a disconnection or if it is replaced by a new cannula. Other methods pertain to automatic purging of the delivery conduit if the elapsed time between successive deliveries of therapeutic gas exceeds a predetermined period of time.

20 Claims, 2 Drawing Sheets

Related U.S. Application Data now Pat. No. 9,108,016, which is a continuation of application No. 13/440,046, filed on Apr. 5, 2012, now Pat. No. 8,944,051.

(51) Int. Cl.
*A61M 16/20* (2006.01)
*A61M 16/00* (2006.01)

(52) U.S. Cl.
CPC .... *A61M 16/0666* (2013.01); *A61M 16/0677* (2014.02); *A61M 16/20* (2013.01); *A61M 16/202* (2014.02); *A61M 2016/003* (2013.01); *A61M 2016/0015* (2013.01); *A61M 2016/0036* (2013.01); *A61M 2202/0275* (2013.01); *A61M 2205/14* (2013.01); *A61M 2205/18* (2013.01); *A61M 2205/3334* (2013.01); *A61M 2205/50* (2013.01); *A61M 2205/502* (2013.01); *A61M 2205/581* (2013.01); *A61M 2205/583* (2013.01); *A61M 2205/6018* (2013.01); *A61M 2205/6054* (2013.01); *A61M 2205/6072* (2013.01)

(56) References Cited

U.S. PATENT DOCUMENTS

| | | |
|---|---|---|
| 5,732,693 A | 3/1998 | Bathe et al. |
| 5,752,504 A | 5/1998 | Bathe |
| 5,865,174 A | 2/1999 | Kloeppel |
| 6,109,260 A | 8/2000 | Bathe |
| 6,125,846 A | 10/2000 | Bathe et al. |
| 6,142,147 A | 11/2000 | Head et al. |
| 6,474,333 B1 | 11/2002 | Heinonen |
| 6,581,592 B1 | 6/2003 | Bathe et al. |
| 7,516,742 B2 | 4/2009 | Stenzler et al. |
| 7,523,752 B2 | 4/2009 | Montgomery et al. |
| 7,762,253 B2 | 7/2010 | Acker et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,431,163 B2 | 4/2013 | Baldassarre et al. |
| 8,573,209 B2 | 11/2013 | Bathe et al. |
| 8,573,210 B2 | 11/2013 | Bathe et al. |
| 8,776,794 B2 | 7/2014 | Bathe et al. |
| 8,776,795 B2 | 7/2014 | Bathe et al. |
| 8,795,741 B2 | 8/2014 | Baldassarre |
| 8,846,112 B2 | 9/2014 | Baldassarre |
| 2002/0058974 A1 | 5/2002 | Van Duren et al. |
| 2005/0004511 A1 | 1/2005 | Figley et al. |
| 2005/0217668 A1 | 10/2005 | Figley et al. |
| 2006/0278222 A1 | 12/2006 | Schermeier et al. |

OTHER PUBLICATIONS

Non-Final Office Action in U.S. Appl. No. 13/440,046, dated Aug. 24, 2012, 16 pages.
Non-Final Office Action in U.S. Appl. No. 13/440,046, dated Jun. 5, 2014, 22 pages.
PCT International Search Report and Written Opinion in PCT/US2013/035079, mailed Jun. 19, 2013, 13 pages.
PCT International Preliminary Report on Patentability in PCT/US2013/035079, mailed Oct. 16, 2014, 9 pages.
INOmax DS (Delivery System): Operation Manual (800 ppm INOMAX (nitric oxide) for Inhalation), Ikaria, Inc. 2010, 112 pages.
INOvent Delivery System: Operation and Maintenance Manual (CGA Variant), Datex-Ohmeda, Inc. 2000, 180 pages.
Using the INOpulse DS Subject Guide, Ikaria, Inc. 2012, 50 pages.
INOmax Label, Nitric Oxide Gas, INO Therapeutics 2013, 2 pages.
INOmax DSIR (Delivery System): Operation Manual (800 ppm INOMAX (nitric oxide) for Inhalation), Ikaria, Inc. 2012, 136 pages.

BREATHING APPARATUS DETECTION AND PURGING

CROSS-REFERENCE TO RELATED APPLICATIONS

This application is a continuation of U.S. patent application Ser. No. 14/394,433, which is the National Phase entry of PCT/US13/35079, filed on Apr. 3, 2013, which is a continuation of U.S. patent application Ser. No. 13/440,046, filed on Apr. 5, 2012, now U.S. Pat. No. 8,944,051, the entire contents of which are incorporated herein by reference in their entirety.

TECHNICAL FIELD

Embodiments of the present invention generally relate to the field of nitric oxide administration, particularly to methods and apparatuses for detecting and purging nasal cannulas and other breathing apparatuses.

BACKGROUND

Nitric oxide (NO) is a gas that, when inhaled, acts to dilate blood vessels in the lungs, improving oxygenation of the blood and reducing pulmonary hypertension. Because of this, nitric oxide is provided as a therapeutic gas in the inspiratory breathing gases for patients with pulmonary hypertension.

However, as NO reacts with oxygen to form nitrogen dioxide ($NO_2$), $NO_2$ can be formed when air is present in the NO delivery conduit. $NO_2$ is a toxic gas which may cause numerous side effects, and the Occupational Safety & Health Administration (OSHA) provides that the permissible exposure limit for general industry is only 5 ppm. Thus, it is desirable to limit exposure to $NO_2$ during NO therapy.

One method of administering NO is through the delivery of a small pulse of a NO-containing gas though a nasal cannula or other conduit. However, the time between successive pulses of therapeutic gas can provide an opportunity for NO and oxygen in the conduit to react to form $NO_2$.

Furthermore, nasal cannulas for portable NO delivery devices may be disconnected intentionally or inadvertently during administration of NO therapy. Such disconnections interrupt therapy and may introduce air into the nasal cannula, which may lead to $NO_2$ formation.

Accordingly, there is a need for new methods and apparatuses for preventing formation of $NO_2$ in the delivery conduit of a nitric oxide delivery apparatus.

SUMMARY

One aspect of the current invention is directed to a method of administering therapeutic gas containing nitric oxide, the method comprising detecting the presence or absence of a nasal or oral breathing apparatus at a connection port of a nitric oxide delivery apparatus, and flowing therapeutic gas containing nitric oxide to the breathing apparatus if the breathing apparatus is determined to be connected to the apparatus and not flowing therapeutic gas containing nitric oxide if the breathing apparatus is determined not to be connected to the apparatus.

According to one or more embodiments of this aspect, an alert is provided if the breathing apparatus is determined not to be connected to the apparatus. The alert may be one or more of an audible alert, a visual alert and a text alert.

In some embodiments, the breathing apparatus is purged when it is first connected, or if it is reconnected after a disconnection. Thus, in some embodiments, the breathing apparatus is purged if the breathing apparatus is determined to be connected to the apparatus after the breathing apparatus is determined not to be connected to the apparatus. The breathing apparatus is purged automatically without patient intervention. In one or more embodiments, the breathing apparatus is purged during patient expiration.

One or more embodiments provide that the breathing apparatus is purged prior to administering the therapeutic gas containing nitric oxide.

In one or more embodiments, detecting the presence or absence of a breathing apparatus comprises sending and receiving signals from the connection port and the breathing apparatus.

Another aspect of the invention pertains to a method of administering therapeutic gas containing nitric oxide, the method comprising: sensing inspiration of a patient, delivering a pulse of therapeutic gas containing nitric oxide to the patient through a valve along a conduit, repeating the delivering a pulse of therapeutic gas to provide successive deliveries, measuring elapsed times between the successive deliveries of therapeutic gas to the patient, determining that an elapsed time between successive deliveries of therapeutic gas exceeds a predetermined period of time, sensing expiration of the patient and purging the conduit during patient expiration. The elapsed time may be reset when the conduit is purged.

In embodiments of this aspect, purging the conduit comprises opening the valve to deliver a pulse of therapeutic gas during patient expiration.

According to some embodiments, one or more patient breaths are detected between successive deliveries of therapeutic gas.

The predetermined time may be in multiple formats, such as a fixed time period or a number of breaths. In some embodiments, the predetermined time is in the range from 5 seconds to 15 seconds. In other embodiments, the predetermined time is in the range from 1 to 10 breaths.

In some embodiments, the conduit comprises a nasal cannula.

Another embodiment provides a nitric oxide delivery apparatus. In embodiments of this aspect, the nitric oxide delivery apparatus comprises a source of therapeutic gas containing nitric oxide, a conduit in fluid communication with the source of therapeutic gas that provides therapeutic gas to a patient, a valve disposed along the conduit that regulates the flow of therapeutic gas through the conduit to the patient, a sensor that detects inspiration and/or expiration of the patient, a timer, and a control system. The control system may be in communication with the timer and the valve, and initiates purging of the conduit during patient expiration when an elapsed time between successive openings of the valve exceeds a predetermined period of time.

In some embodiments, the control system further comprises a CPU and a computer-readable medium having stored thereon a set of machine-executable instructions that, when executed by the CPU, cause the apparatus to perform a method comprising: detecting inspiration of the patient; opening the valve to deliver a pulse of therapeutic gas through a conduit to the patient during inspiration; measuring elapsed times between successive valve openings; determining that an elapsed time between successive valve openings exceeds a predetermined period of time; detecting expiration of the patient; and purging the conduit during patient expiration. Purging the conduit may comprise opening the valve to deliver a pulse of therapeutic gas during patient expiration. Furthermore, one or more patient breaths may be detected between successive valve openings.

The predetermined time may be in multiple formats, such as a fixed time period or a number of breaths. In some embodiments, the predetermined time is in the range from 5 seconds to 15 seconds. In other embodiments, the predetermined time is in the range from 1 to 10 breaths.

In some embodiments of this aspect, the conduit comprises a nasal cannula.

Various embodiments are listed above and will be described in more detail below. It will be understood that the embodiments listed may be combined not only as listed below, but in other suitable combinations in accordance with the scope of the invention.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Provided are methods and apparatuses for administering nitric oxide to a patient, which help prevent the formation of $NO_2$ and the inadvertent administration of $NO_2$ to the patient. One aspect of the current invention pertains to a method that comprises providing a valve intermediate a source of therapeutic gas containing nitric oxide and a patient, sensing inspiration of the patient, and opening the valve to deliver a pulse of therapeutic gas through a conduit to the patient during inspiration. In order to prevent $NO_2$ formation, the elapsed time between successive pulsed deliveries of therapeutic gas to the patient is measured and compared to a predetermined time, which may be related to the rate of $NO_2$ formation. If the elapsed time between successive deliveries of therapeutic gas exceeds this predetermined period of time, then the conduit is purged. According to one or more embodiments of this method, the conduit is purged during patient expiration so that the $NO_2$ is not administered to the patient.

Figure 1:
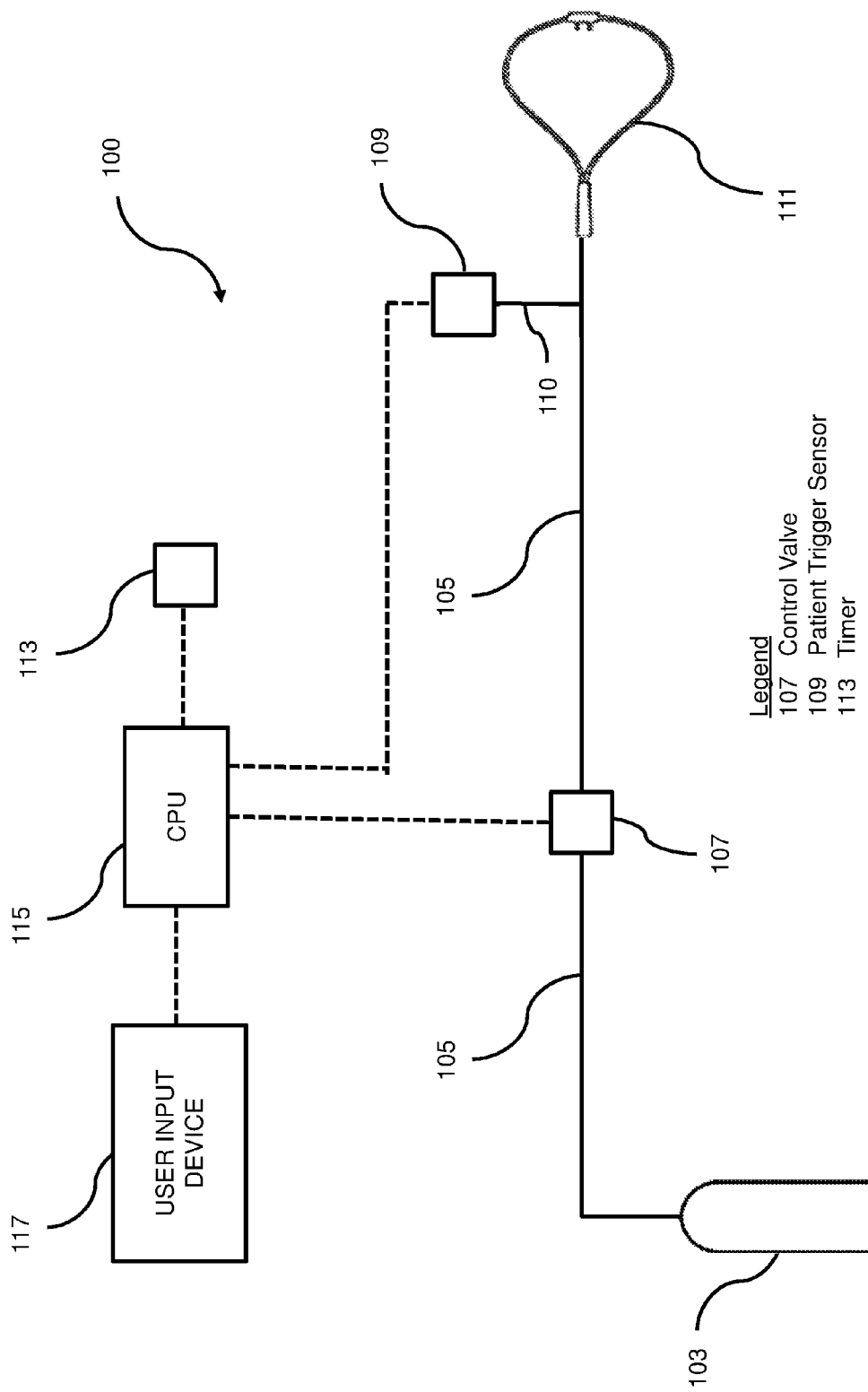
FIG. 1 illustrates a nitric oxide delivery apparatus in accordance with one or more embodiments.

FIG. 1 shows an exemplary nitric oxide delivery apparatus 100 for carrying out certain embodiments of the nitric oxide administration method. A source of therapeutic gas containing nitric oxide may include gas storage cylinder 103. Exemplary cylinders may contain NO in a carrier gas such as nitrogen, with a NO concentration ranging from 1 ppm to 20,000 ppm, such as from 5 ppm to 10,000 ppm, or from 10 ppm to 5,000 ppm. According to one or more embodiments, the cylinder concentration is in the range from 100 ppm to 8,000 ppm. In some embodiments, the cylinder concentration is in the range from 100 ppm to 4,500 ppm, such as from 200 ppm to 4,200 ppm, or 500 ppm to 4,000 ppm, or 800 ppm to 3,800 ppm, or 1,000 ppm to 3,600 ppm, or 1,200 ppm to 3,400 ppm, or 1,400 ppm to 3,200 ppm, or 1,600 ppm to 3,000 ppm, or 1,800 ppm, to 2,800 ppm, or 2,000 ppm to 2,600 ppm, or 2,200 ppm to 2,500 ppm, In some embodiments, the cylinder concentration is in the range from 100 ppm to 10,000 ppm, such as from 500 ppm to 9,000 ppm, or 1,000 ppm to 8,000 ppm, or 2,000 ppm to 7,000 ppm, or 3,500 ppm to 6,000 ppm, or 4,000 ppm, to 5,500 ppm, or 4,400 ppm to 5,200 ppm, or 4,600 ppm to 5,000 ppm, In one or more embodiments, the cylinder concentration is about 2440 ppm or about 4880 ppm.

Gas storage cylinder 103 is in fluid communication with conduit 105, which carries the therapeutic gas from gas storage cylinder 103 to the patient. The conduit 105 may comprise a nasal cannula or other nasal or oral breathing apparatus 111 for delivering the therapeutic gas to the patient. In addition, conduit 105 may comprise a gas hose or tubing section, a pressure regulator, and a delivery manifold, etc. Although specific reference is made to nasal cannulas, other types of nasal or oral breathing apparatuses may be used, such as breathing masks. One or more control valves 107 regulate the flow of therapeutic gas through the conduit 105 to the patient. A passageway 110 is in fluid communication with the conduit 105 which connects a patient trigger sensor 109 to the conduit 105. The signal from the patient trigger sensor 109 may be further processed via hardware and/or software logic by CPU 115, and detects when a patient begins inspiration or expiration, and may provide that information to a control system. In this description, patient trigger sensor 109 refers to the patient trigger sensor and any logic processing algorithms which may be incorporated into the system. In some embodiments, the patient trigger sensor 109 may be used to determine the patient's inspiration by detecting a negative pressure caused by the patient's breathing effort. Similarly, the patient trigger sensor 109 may detect the patient's expiration by detecting a positive pressure caused by the patient. Alternatively, the patient trigger sensor 109 may be a flow sensor that measures the flow through conduit 105.

The control system may comprise one or more central processing unit(s) (CPU) 115 in communication with control valve 107 and the patient trigger sensor 109. When the patient trigger sensor 109 determines that a patient is beginning inspiration, the CPU 115 sends a signal to the control valve 107 to open the control valve 107 to deliver a pulse of therapeutic gas. Control valve 107 is only open for a certain period of time, and the length of the time period, as well as the amount which the control valve 107 opens, will determine the volume of the pulse of therapeutic gas. For example, when control valve 107 is open for a longer period of time, the amount of therapeutic gas in the pulse increases. In certain embodiments, the pulse size may vary from one pulse to the next so that the total amount of therapeutic gas administered over a given time interval is constant, even though a patient's breathing rate may change during this interval. Multiple valves may also be used to deliver the pulse at various flow rates. Alternatively, a proportional valve may be used which allows variable control of flow rate.

However, the time period between successive pulses of therapeutic gas may allow $NO_2$ to form in the conduit 105 or the nasal cannula 111. For example, the therapeutic gas may not be pulsed for a certain period of time because patient trigger sensor 109 may not detect a breath, or a breath may be skipped due to an intermittent pulse dosing regimen. Alternatively, a breath may be skipped because the amount to be delivered on a particular breath is lower than a minimum threshold amount that the apparatus can deliver.

To prevent $NO_2$ formation between successive pulses of therapeutic gas, the apparatus may include a timer 113, which may be integrated into the CPU 115, that measures the time elapsed between successive openings of the control valve 107. The control system is in communication with the timer 113 and determines when the elapsed time exceeds a predetermined time. This predetermined time may be calculated based on the concentration of NO, the expected amount of air in the conduit 105 or the nasal cannula 111, and the maximum allowable $NO_2$ concentration. According to one or more embodiments, the predetermined time is in the range from 2 seconds to 20 seconds. In some embodiments, the predetermined time is in the range from 5 seconds to 15 seconds.

In some embodiments, one or more patient breaths are detected between successive pulses. In these embodiments, administration during one or more patient breaths is skipped. This may be for a variety of reasons, such as the device being configured not to dose on every breath as part of an intermittent pulsing regimen, or the dose being set low enough that the amount to be delivered during a particular breath is instead added to the dose delivered during one or more subsequent breaths.

In one or more embodiments, the predetermined time is specified as a number of breaths. For example, if the predetermined period of time is one breath, then the device may be purged every breath that NO is not delivered to the patient. The purging may also occur during breaths on which NO is delivered, such as during expiration after the pulsed NO dose is delivered to the patient. In one or more embodiments, the predetermined time is in the range from 1 to 10 breaths. According to some embodiments, the predetermined time is in the range from 1 to 5 breaths. Some embodiments provide that the predetermined time is in the range from 1 to 3 breaths. Other embodiments provide that the predetermined time is in the range from 2 to 5 breaths.

When the control system determines that the elapsed time exceeds the predetermined time, the control system purges the conduit 105 and/or the nasal cannula 111. According to one or more embodiments, the conduit and/or nasal cannula is purged during expiration so that the purged gas is directed away from the patient. Thus, the control system may wait until the patient trigger 109 detects patient expiration before purging. In some embodiments, purging the conduit 105 and/or the nasal cannula 111 comprises opening the control valve 107 to deliver a pulse of therapeutic gas during patient expiration. In some embodiments, the pulse of gas may be very small—only enough volume to purge the cannula nares, or large enough to purge the entire cannula—filling it with fresh therapy gas. Accordingly, in some embodiments, the purge volume is less than the total internal volume of the cannula. For example, the purge volume may be less than or equal to any of the following percentages of the nasal cannula internal volume: 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, 0.5%, 0.25%, 0.2%, 0.15% or 0.1%. Likewise, the purge volume may be less than or equal to any of the following volumes: 20 mL, 15 mL, 10 mL, 9 mL, 8 mL, 7 mL, 6 mL, 5 mL, 4 mL, 3 mL, 2 mL, 1 mL, 0.75 mL, 0.5 mL, 0.4 mL, 0.3 mL, 0.2 mL, 0.1 mL or 0.05 mL. It may be advantageous to purge with only a small volume of gas (such as any of the percentages or volumes listed above) because the volume may be large enough to purge the cannula nares where $NO_2$ may form, but not waste therapy gas for an entire purge of the nasal cannula. In other embodiments, instead of using the control valve 107 to purge, a separate purge system is used to purge the conduit 105 and/or the nasal cannula 111. A valve mounted on the conduit upstream of the nasal cannula may be used to purge the conduit independently of the cannula. Once the conduit 105 and/or the nasal cannula 111 has been purged, the timer may be reset.

The CPU 115 may be in communication with a user input device 117. This user input device 117 can receive desired settings from the user, such as the patient's prescription in mg/kg/hr or mg/kg/breath, patient's age, height, sex, weight, etc.

The CPU 115 may also be in communication with a flow sensor (not shown), which would measure the flow of therapeutic gas through control valve 107. The CPU 115 can be coupled to a memory (not shown) and may be one or more of readily available memory such as random access memory (RAM), read only memory (ROM), flash memory, compact disc, floppy disk, hard disk, or any other form of local or remote digital storage. Support circuits (not shown) can be coupled to the CPU 115 to support the CPU 115, sensors, control valves, etc. in a conventional manner. These circuits include cache, power supplies, clock circuits, input/output circuitry, subsystems, power controllers, signal conditioners, and the like.

The memory may store a set of machine-executable instructions (or algorithms) for calculating the desired volume of the gas pulse and the pulsing schedule to achieve a particular patient prescription. For example, if the patient's breathing rate and the cylinder concentration are known, then the CPU 115 can calculate how much volume of therapeutic gas needs to be administered each breath or set of breaths to provide the desired dosage of nitric oxide. The memory may also record the time that the control valve 107 is open during each pulse, so that future calculations can take into account how much nitric oxide has previously been administered.

In some embodiments, the set of machine-executable instructions (or algorithms), when executed by the CPU 115, cause the apparatus to perform a method comprising detecting inspiration of the patient, opening the valve to deliver a pulse of therapeutic gas through a conduit to the patient during inspiration, timing elapsed times between successive valve openings, determining that an elapsed time between successive valve openings exceeds a predetermined period of time, detecting expiration of the patient, and purging the conduit during patient expiration. The machine-executable instructions may also comprise instructions for any of the other methods described herein.

Another aspect of the current invention provides a method of administering therapeutic gas containing nitric oxide, the method comprising determining whether a nasal or oral breathing apparatus is connected to a nitric oxide delivery apparatus and administering therapeutic gas containing nitric oxide to a patient if the breathing apparatus is determined to be connected to the apparatus and not administering therapeutic gas if the breathing apparatus is determined not to be connected to the apparatus. As used herein, a breathing apparatus refers to a nasal or oral apparatus for delivering breathing gas or therapeutic gas directly to a patient, such as a nasal cannula or breathing mask.

Figure 2:
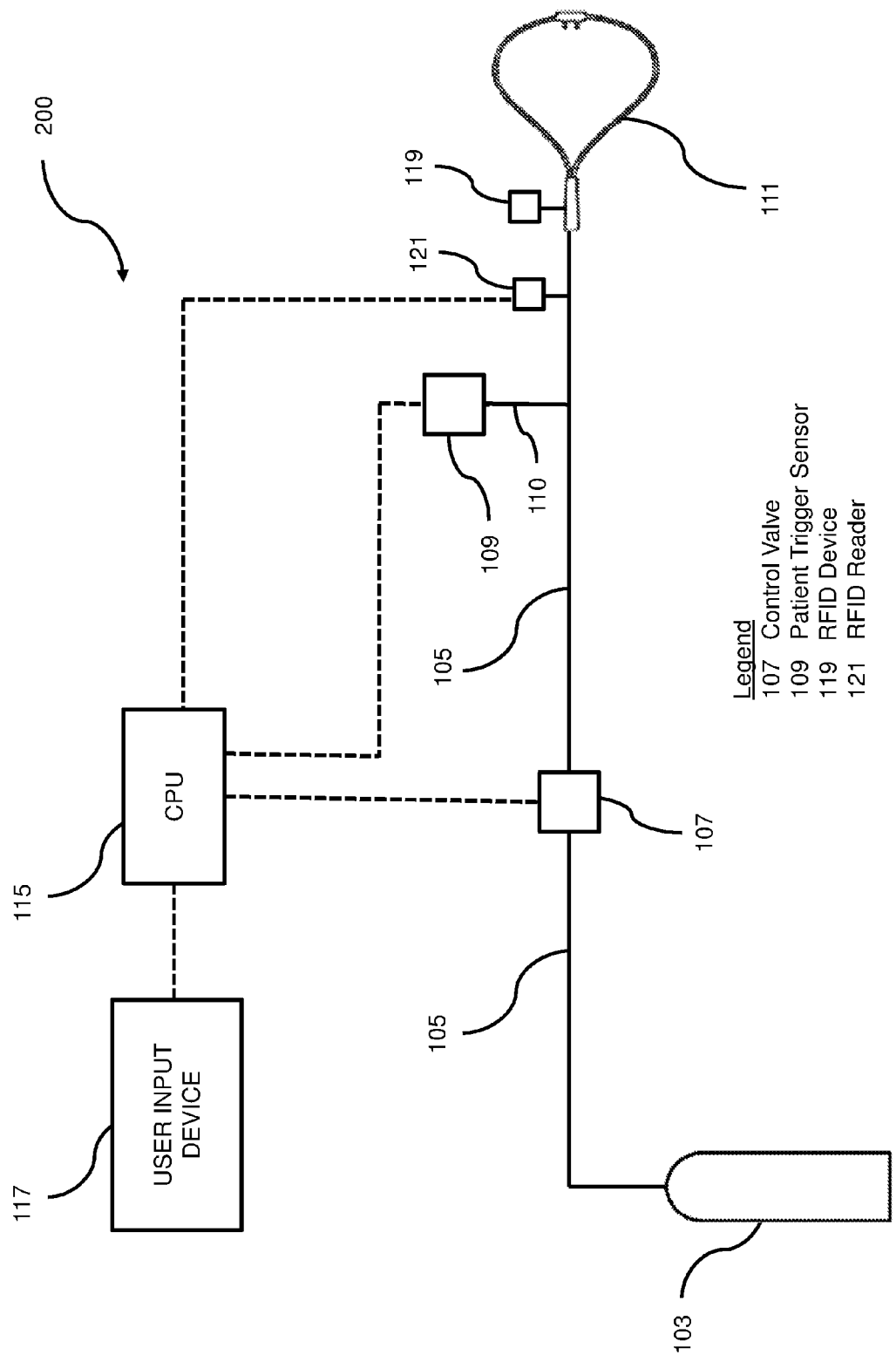
FIG. 2 illustrates a nitric oxide delivery apparatus in accordance with one or more embodiments.

FIG. 2 shows an exemplary nitric oxide delivery apparatus 200 for carrying out certain embodiments of this aspect. According to one or more embodiments, an apparatus for performing this method may have any of the features described for the first aspect. In one or more embodiments, the control system of the nitric oxide delivery apparatus may determine whether a breathing apparatus 111 is connected to the apparatus. In the embodiment shown in FIG. 2, the breathing apparatus is a nasal cannula. In some embodiments, the control system determines whether a nasal cannula 111 is connected to the apparatus by detecting the presence or absence of the nasal cannula 111 at a connection port of the apparatus. For example, as shown in FIG. 2, a sensor 121 at or near the connection port may be used to detect the presence or absence of the nasal cannula 111. The sensor 121 then sends a signal to the CPU 115 indicating whether the nasal cannula 111 is connected to the apparatus.

This detection may be performed in a variety of ways, such as by short range radio frequency identification (RFID), a light source/photodiode arrangement, strain gauge, or a proximity sensor, bar code, or a switch (of various types) which state changes when the cannula is present. Alternatively, the nitric oxide delivery apparatus may determine that a nasal cannula is connected by sensing an increase in back-pressure of a purge delivered through the cannula when the cannula is connected. The sensor 121 may send and receive signals from the nasal cannula 111. If RFID is used, the sensor 121 may be a RFID reader and the nasal cannula may have a RFID device 119 that transmits a radio frequency from the RFID device 119 to the RFID reader 121.

When the nasal cannula 111 is determined to be connected to the apparatus, then the apparatus may administer the therapeutic gas containing nitric oxide to the patient. When the nasal cannula 111 is determined not to be connected to the apparatus, the apparatus may prevent the administration of therapeutic gas. Thus, an intentional or inadvertent disconnection of the nasal cannula 111 may stop the delivery of therapeutic gas through the conduit 105.

If the nasal cannula 111 is not connected, the apparatus may provide an alert to a user of the apparatus, such as the patient or medical personnel. An alert may also be provided if a nasal cannula is partially or incorrectly attached to the apparatus, or if there is a leak at the apparatus/cannula connection. In some embodiments, the alert includes one or more of an audible alert, a visual alert and a text alert. The alerts may be provided directly at the apparatus, or may be provided to a remote location, such as to a cellular phone, computer, or other remote device.

If the nasal cannula 111 is reconnected after a disconnection, or if the nasal cannula 111 is replaced, it may be necessary to purge the nasal cannula 111 to prevent the formation of $NO_2$ or remove any $NO_2$ that formed during the disconnection, or to fill a new cannula containing air with therapy gas. Thus, if the apparatus determines that the nasal cannula 111 is connected after the nasal cannula is determined not to be connected, then the control system may purge the nasal cannula 111. The nasal cannula may also be purged at apparatus start-up. Any of these purging procedures may be automatic, i.e. without patient intervention. As with the purging described above, in some embodiments, the cannula 111 is purged during patient expiration to direct the purged gases away from the patient. According to one or more embodiments, the therapeutic gas is not administered to the patient until after the nasal cannula 111 is purged.

The control system may comprise a set of machine-executable instructions (or algorithms), when executed by the CPU 115, cause the apparatus to perform a method comprising determining whether a nasal cannula is connected to the nitric oxide delivery apparatus by detecting the presence or absence of the nasal cannula at a connection port of the nitric oxide delivery apparatus, and administering therapeutic gas containing nitric oxide to the patient if the nasal cannula is determined to be connected to the apparatus and not administering therapeutic gas containing nitric oxide if the nasal cannula is determined not to be connected to the apparatus. According to one or more embodiments, the machine-executable instructions further comprise instructions to provide an alert if the nasal cannula is determined not to be connected to the apparatus. In some embodiments, the machine-executable instructions further comprise instructions to purge the cannula if the cannula is determined to be connected to the apparatus after the cannula is determined not to be connected to the apparatus. The machine-executable instructions may also comprise instructions for any of the other methods described herein.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of administering therapeutic gas containing nitric oxide, the method comprising:
    sensing inspiration of a patient;
    during patient inspiration, delivering a pulse of the therapeutic gas containing nitric oxide through one or more valves along a conduit and subsequently through a nasal cannula having one or more nares to the patient;
    measuring an elapsed time since the last delivery of the therapeutic gas to the patient;
    determining that the elapsed time exceeds a predetermined period of time; and
    purging the nasal cannula with a purge volume greater than a volume of the one or more nares and less than a total internal volume of the nasal cannula.

2. The method of claim 1, wherein purging the nasal cannula comprises opening one of the one or more valves to deliver a pulse of the therapeutic gas during patient expiration.

3. The method of claim 1, wherein one or more patient breaths are detected between successive deliveries of the therapeutic gas.

4. The method of claim 1, wherein the elapsed time is reset when the nasal cannula is purged.

5. The method of claim 1, wherein the predetermined period of time is in a range from 5 seconds to 15 seconds.

6. The method of claim 1, wherein the predetermined period of time is in a range from 1 to 10 breaths.

7. The method of claim 1, wherein the predetermined period of time is in a range from 2 to 20 seconds.

8. The method of claim 1, wherein the purge volume is less than or equal to 1 mL.

9. The method of claim 1, wherein the purge volume is less than or equal to 0.5 mL.

10. A method of administering therapeutic gas containing nitric oxide, the method comprising:
   delivering a pulse of the therapeutic gas containing nitric oxide to a patient via a nasal cannula having one or more nares;
   determining that an elapsed time since the last delivery of the therapeutic gas exceeds a predetermined period of time; and
   purging the nasal cannula with a purge volume greater than a volume of the one or more nares and less than a total internal volume of the nasal cannula.

11. The method of claim 10, wherein purging the nasal cannula comprises opening one or more valves to deliver a pulse of the therapeutic gas during patient expiration.

12. The method of claim 10, wherein one or more patient breaths are detected between successive deliveries of the therapeutic gas.

13. The method of claim 10, wherein the elapsed time is reset when the nasal cannula is purged.

14. The method of claim 10, wherein the predetermined period of time is in a range from 2 to 20 seconds.

15. The method of claim 10, wherein the predetermined period of time is in a range from 5 seconds to 15 seconds.

16. The method of claim 10, wherein the predetermined period of time is in a range from 1 to 10 breaths.

17. The method of claim 10, wherein the purge volume is less than or equal to 1 mL.

18. The method of claim 10, wherein the purge volume is less than or equal to 0.5 mL.

19. A nitric oxide delivery apparatus comprising:
   a source of therapeutic gas containing nitric oxide;
   a conduit in fluid communication with the source of the therapeutic gas;
   one or more valves disposed along the conduit that regulate a flow of the therapeutic gas through the conduit;
   a nasal cannula comprising one or more nares in fluid communication with the conduit that provides the therapeutic gas to a patient;
   a sensor that detects inspiration and/or expiration of the patient;
   a timer; and
   a control system in communication with the timer and the one or more valves that initiates purging of the nasal cannula when an elapsed time since the last delivery of the therapeutic gas exceeds a predetermined period of time, wherein the nasal cannula is purged with a purge volume greater than a volume of the one or more nares and less than a total internal volume of the nasal cannula.

20. The nitric oxide delivery apparatus of claim 19, wherein the purge volume is less than or equal to 1 mL.

* * * * *